(12) United States Patent
Nagaoka et al.

(10) Patent No.: US 7,811,451 B2
(45) Date of Patent: Oct. 12, 2010

(54) SEPARATION COLUMN AND LIQUID CHROMATOGRAPH USING THE SAME

(75) Inventors: Yoshihiro Nagaoka, Ishioka (JP); Masahito Ito, Hitachinaka (JP); Daizo Tokinaga, Hachiohji (JP); Tomohiro Shoji, Hitachinaka (JP); Tomonari Morioka, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/877,944

(22) Filed: Oct. 24, 2007

(65) Prior Publication Data
US 2008/0099389 A1    May 1, 2008

(30) Foreign Application Priority Data
Oct. 25, 2006   (JP)   ............... 2006-289415

(51) Int. Cl.
*B01D 15/08* (2006.01)
*C02F 1/28* (2006.01)
*G01N 30/02* (2006.01)

(52) U.S. Cl. ............. 210/198.2; 210/656; 422/70; 73/61.52

(58) Field of Classification Search ............. 210/198.2, 210/656; 422/70; 73/61.52
See application file for complete search history.

(56) References Cited

U.S. PATENT DOCUMENTS

| | | | | |
|---|---|---|---|---|
| 5,972,222 A | * | 10/1999 | Gjerde et al. | 210/635 |
| 6,652,745 B2 | * | 11/2003 | Gjerde et al. | 210/198.2 |
| 6,797,174 B2 | * | 9/2004 | Neuroth et al. | 210/656 |
| 2005/0169829 A1 | * | 8/2005 | Dai et al. | 423/445 R |

FOREIGN PATENT DOCUMENTS

| | | |
|---|---|---|
| EP | 0 990 153 B1 | 4/2000 |
| JP | 11-064314 | 3/1999 |
| JP | 2002-505005 A | 2/2002 |
| JP | 2003-530571 | 10/2003 |

OTHER PUBLICATIONS

Liang, C., et al. A graphitized-carbon monolithic column. Anal. Chem. vol. 75, 2003: 4904-4912.*

* cited by examiner

*Primary Examiner*—Krishnan S Menon
*Assistant Examiner*—Katherine Zalasky
(74) *Attorney, Agent, or Firm*—Mattingly & Malur, P.C.

(57) ABSTRACT

The flow rate of a solvent is reduced as a separation column and the separation performance is improved even under high-pressure conditions. There is provided a separation column including a monolith rod into which a sample and a mobile phase flow, the separation column comprising: a coating material coated on the outer circumference of a monolith rod; a support member into which the monolith rod coated with the coating material is inserted, and a rod fixing material fitted into or filled a gap between the coating material and the support member; wherein the upper end face of the rod fixing material is sealed, the upper end face being the inflow-side end when the separation column is assembled.

7 Claims, 6 Drawing Sheets

SEPARATION COLUMN AND LIQUID CHROMATOGRAPH USING THE SAME

BACKGROUND OF THE INVENTION

1. Field of the Invention

The present invention relates to a separation column which is used for separating components in a liquid sample, the separation column being used for a high performance liquid chromatograph or the like, and to a liquid chromatograph apparatus using the same. In particular, the present invention is suitable for reducing the analysis time.

2. Description of the Related Art

A monolith column is employed for use in a conventional high performance liquid chromatograph or the like. In this case, the monolith column has an integrated structure of a three-dimensional network skeleton and relevant void (flow path, macro pores, and through pores), unlike the particle-packed column commonly used. The use of such a monolith column enables a column to have a large porosity and accordingly a nonincreasing flow resistance although the surface area increases. For example, performance has been improved with the use of a monolith column having a porous material (monolith rod or monolithic silica rod) implemented in a capillary.

Further, since it is difficult to form the outer diameter, curving, etc. of a porous material with high accuracy, gap is likely to occur between the capillary and the porous material. It is known that a resin coating material is provided on the outer circumferential surface of the porous material in order to prevent leakage of a mobile phase from the side face of the column. Such a technique is disclosed, for example, in JP-A-11-64314.

Further, it is known that monolithic molding is introduced in a fiber-reinforced plastic pipe and then the pipe is heated in order to improve the contact between the column unit and a monolithic adsorbent. Such a technique is disclosed, for example, in JP-A-2003-530571.

SUMMARY OF THE INVENTION

In accordance with the technique disclosed in JP-A-11-64314, a resin coating material is only provided on the outer circumferential surface of a porous material. Therefore, a liquid flowing into the column comes into contact with the resin at the end of the column, and a volatile solvent in the resin agent elutes off during column-based analysis, which may degrade the separation performance.

In accordance with the technique disclosed in JP-A-2003-530571, monolithic molding becomes hot at the time of heating. Therefore, with a monolithic adsorbent packed with a filling agent having a chemical bond of the octadecylsilyl group to the silica gel support, the octadecylsilyl group etc. are removed, resulting in degradation of the separation performance of the column. Further, the influence of heating is significant at the periphery. The thinner monolithic molding is made in order to reduce the flow rate of the solvent, the more the separation performance of the column degrades.

Further, in accordance with the techniques disclosed in JP-A-11-64314 and JP-A-2003-530571, a monolith rod having a diameter of 4 mm or 4.6 mm is used, which is similar to the diameter (about 5 mm) of the filled section of the conventional particle-packed column. When the monolithic rod is used to increase the porosity and the liquid flow velocity is increased to reduce the analysis time, the consumption of the mobile phase increases.

An object of the present invention is to solve the above-mentioned subjects of conventional arts, making it possible to use a thinner porous material to reduce the flow rate of the solvent as a separation column, and accordingly preventing the degradation of the separation performance even with smaller flow rates. Further, another object of the present invention is, in particular, to prevent the elution of chemical components from the column and leakage thereof at high pressure, thereby reducing the analysis time while maintaining high analysis performance.

In order to accomplish the above-mentioned object, a monolith type separation column according to the present invention includes a monolith rod which is cylindrically formed with a porous material and into which a sample and a mobile phase flow, the separation column comprising: a coating material coated on the outer circumference of the above-mentioned monolith rod; a support member into which the monolith rod coated with the coating material is inserted; and a rod fixing material fitted or packed into a gap between the coating material and the support member; wherein the upper end face of the rod fixing material is sealed, the upper end face being the inflow-side end when the separation column is assembled.

Further, a liquid chromatograph according to the present invention uses a monolith type separation column including a monolith rod into which a sample and a mobile phase flow, wherein the separation column comprises: the monolith rod cylindrically formed with a porous material; a coating material coated on the outer circumference of the monolith rod; a support member into which the monolith rod coated with the coating material is inserted; and a rod fixing material fitted or packed into a gap between the coating material and the support member; and wherein the maximum pressure of the mobile phase flowing into the monolith rod is set to 5 to 30 MPa.

Further, a liquid chromatograph according to the present invention uses a monolith type separation column including a monolith rod into which a sample and a mobile phase flow, wherein the separation column comprises: the monolith rod cylindrically formed with a porous material; a coating material coated on the outer circumference of the monolith rod; a support member into which the monolith rod coated with the coating material is inserted; and a rod fixing material fitted or packed into a gap between the coating material and the support member; and wherein the upper end face of the rod fixing material is sealed, the upper end face being the inflow-side end when the separation column is assembled.

In accordance with the present invention, a rod fixing material is fitted or packed into a gap between a monolith rod coated with a coating material and a support member thereof, and the upper end face of the rod fixing material is sealed. This makes it possible to reduce the flow rate of a solvent as a separation column and prevent the degradation of the separation performance even with smaller flow rates. Further, in a liquid chromatograph, the present invention makes it possible to reduce the analysis time and prevent the elution of chemical components from the column and the leakage thereof at high pressure.

DETAILED DESCRIPTION OF PREFERRED EMBODIMENTS

In a conventional high performance liquid chromatograph or the like, it is necessary to increase the amount of liquid fed per unit time in order to reduce the analysis time with the generally used particle-packed column. In order to maintain the separation performance, it is necessary to reduce the diameter of packed particles to increase the surface area thereof. Even if the analysis time is reduced to 1/10 by reducing the particle diameter to about 2 μm with respect to the conventional column in which a cylindrical vessel having an internal diameter of about 4 mm is filled with particles having a diameter of about 5 μm, the flow resistance increases making it necessary to feed the liquid at high pressure.

Therefore, a monolith type separation column based on a monolith rod cylindrically formed with a porous material is used for a liquid chromatograph.

Figure 1:
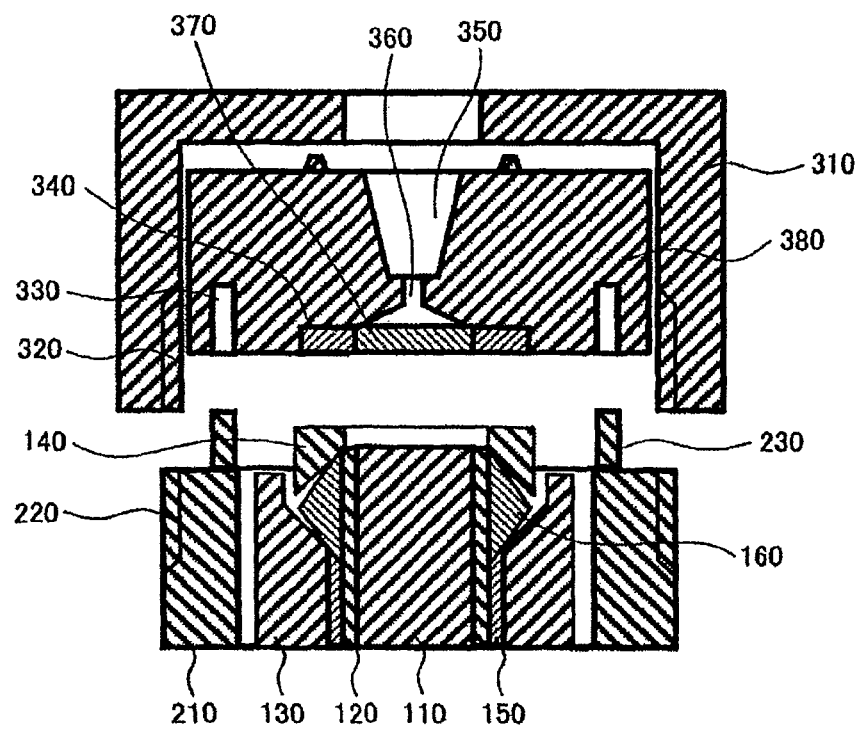
FIGS. 1A and 1B are sectional views on the sample inflow side of a separation column according to an embodiment of the present invention.
Figure 1:
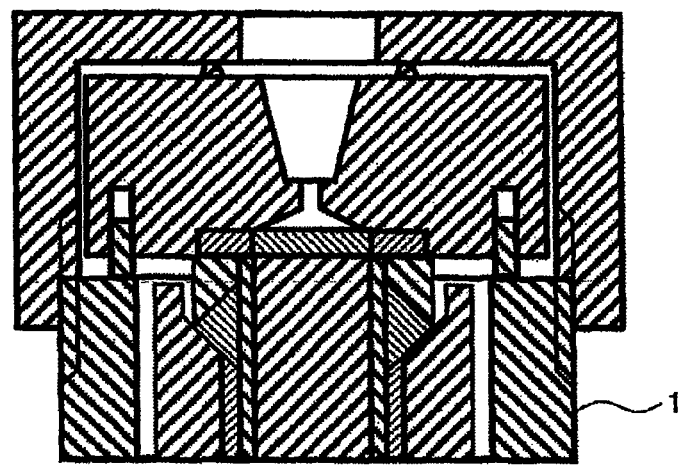

FIGS. 1A and 1B show sectional views on the sample inflow side of a separation column. Since the separation column is vertically symmetric, i.e., the inflow and outflow sides have the same structure, FIG. 1 shows only a half (inflow side) of the separation column.

A monolith rod (monolithic silica rod) 110 cylindrically formed with a porous material is coated with a coating material 120 and inserted into a support member (capillary) 130 made of, for example, a stainless material to improve the strength. In particular, in order to obtain a liquid chromatograph apparatus that can be used even if the maximum pressure of the mobile phase flowing into the separation column is 5 to 30 MPa or more and reduces the analysis time, the diameter of the monolith rod 110 is set to 1.2 to 2.8 mm, desirably to 2 mm or less. The length in the flow direction, i.e., the length of a separation column 1, ranges from 30 mm to 200 mm depending on the sample to be separated. Therefore, it is desirable to prepare three different monolith rods 110 having a diameter of 2 mm and a length of 30 mm, 50 mm, and 100 mm.

Further, when the liquid is fed under the same pressure with a constant cross-sectional area through which the liquid passes, i.e., with a constant porosity, the amount of liquid fed per unit time, i.e., the consumption of the mobile phase is in inverse proportion to the cross-sectional area of the monolith rod. Therefore, the use of a monolith rod with a diameter of 2 mm or less makes it possible to reduce the consumption of the mobile phase to 1/4 in comparison with the use of a monolith rod with a diameter of about 4 mm. Therefore, it is possible to obtain a usable column that can actually be used in a region with a flow rate of 1.0 ml/min or less used by diverse general-purpose high performance liquid chromatograph apparatuses.

The gap between the coating material 120 and the support member 130 is filled with a rod fixing material 150. A sealing member 160 is fitted to both ends (the inflow-side end in FIG. 1) of the monolith rod 110 coated with the coating material 120 so that a push-on holder 140 can move vertically.

An outer holder 210 is provided on the outer circumferential side of the support member 130. When a fixing member 310 is rotated with respect to the outer holder 210, threaded portions 320 and 220 are fastened so that a packing 340 provided in a connecting member 380 be pressed against the push-on holder 140. Since a projection 230 provided at the end of the outer holder 210 is positioned at a depression 330 provided on the connecting member 380, the connecting member 380 remains still even if the fixing member 310 is rotated, i.e., the packing 340 is pressed against the push-on holder 140 without being rotated.

FIG. 1A shows a condition before the threaded portions 320 and 220 are fastened, i.e., before the separation column 1 is assembled. The lower figure of FIG. 1 shows a condition after threaded portions 320 and 220 are fastened, i.e., when the separation column 1 has been assembled.

In FIG. 1B, the packing 340 is pressed against the push-on holder 140 that is then compressed to press the sealing member 160 against the support member 130. For the push-on holder 140, the outer circumference is made thicker than the inner circumference to form a slanted lower surface. For the sealing member 160, the inner circumference is made higher than the outer circumference to form a reversely slanted upper surface. Therefore, if the packing 340 slightly moves at the assembly time, the sealing member is certainly pressed toward the inner circumference side because of wedge effect.

An inflow pipe (not shown) is connected to a connecting section 350 of the connecting member 380, and then a sample to be separated and a mobile phase flow into the separation column 1 from an inlet 360. Then, after passing through a diffusion member 370 and radially diffusing, the sample and the mobile phase flow into the monolith rod 110 and then move toward the outflow side (downward direction of the figure) while repeating adsorption and desorption. In this process, the sample is separated for each chemical component which is then detected by a detector (not shown) located downstream of the outlet of the separation column.

As the coating material 120, it is preferable to use a heat shrinkable tube having an inner diameter that becomes larger than the outer diameter of the monolith rod 110 at the normal temperature and smaller than the same when heated. It may also be possible that coating is made with a fluid resin material, glass, metallic evaporation, or the like.

Since the monolith rod 110 has an unevenness of several micrometers to several tens of micrometers on the outer circumferential surface in contact with the coating material 120, an elastic or fluid material that absorbs the unevenness to come into contact with the surface is suitable as the coating material 120. Further, in order to cause the liquid to flow to the monolith rod 110 under high pressure, it is desirable that the coating material be made thin or a high-modulus material be selected to prevent a gap from being formed by deformation.

As the rod fixing material 150, it is preferable to fit a silicon rubber or fill with fluid rubber or resin, a thermoset resin, glass, or metal; and then subject the material to dry hardening at such a low temperature that the octadecylsilyl group etc. are not removed, for example, at about 200° C. Further, like the coating material 120, in order to cause the liquid to flow to the monolith rod 110 under high pressure, it is desirable that the filling gap be minimized or a high-modulus material be selected to prevent a gap from being formed by deformation.

As the sealing member 160, it is preferable to use a molded product, PTFE (e.g., TEFLON (registered trademark)) or fluoride rubber processed after molding, or a highly chemical-resistant resin or rubber such as perfluoroelastomer.

The inner circumference of the packing 340 is composed of the diffusion member 370 which is used to introduce the sample into the monolith rod 110 while diffusing the sample. It is desirable that the outer diameter of the diffusion member 370, i.e., the inner diameter of the packing 340, be almost equal to or slightly smaller than the outer diameter of the monolith rod, more specifically, at least 0.8 times and at most 1.2 times the outer diameter of the monolith rod 110. With this condition, the liquid flowing into the column does not come into contact with the rod fixing material 150 at the upper end, preventing the degradation of the separation performance.

Since the high-pressure liquid flowing into the monolith rod 110 is sealed by a combination of the packing 340 and the push-on holder 140 and a combination of the push-on holder 140 and the sealing member 160, the liquid does not leak outside the separation column 1. Further, since the sealing member 160 is compressed by the push-on holder 140 and the support member 130 to be firmly attached to the coating material 120, the upper end faces of the rod fixing material 150 do not come into contact with the liquid. Accordingly, there is no risk that a volatile solvent in the rod fixing material 150 elutes off or the separation performance is degraded during column-based analysis.

Since it is necessary to fill a tight gap with the rod fixing material 150, it needs to be dissolved with the solvent. Although the rod fixing material is subjected to dry hardening after filling, the solvent tends to remain in the tight gap and elutes off affecting the performance during analysis. Therefore, the gap is sealed by the sealing member 160 to prevent the liquid from coming in contact with the rod fixing material 150. On the other hand, as the sealing member 160, it is preferable to fit a molded member or a member processed after molding at the end of the monolith rod 110 coated with the coating material 120 making it possible to select a highly chemical-resistant material.

Therefore, in the manufacturing process of the separation column 1, it is possible to manufacture a separation column at such a low temperature that the octadecylsilyl group etc. are removed and prevent the elution of chemical components from the rod fixing material 150 packed into the gap between the monolith rod 110 coated with the coating material 120 and the support member 130.

Figure 2A:
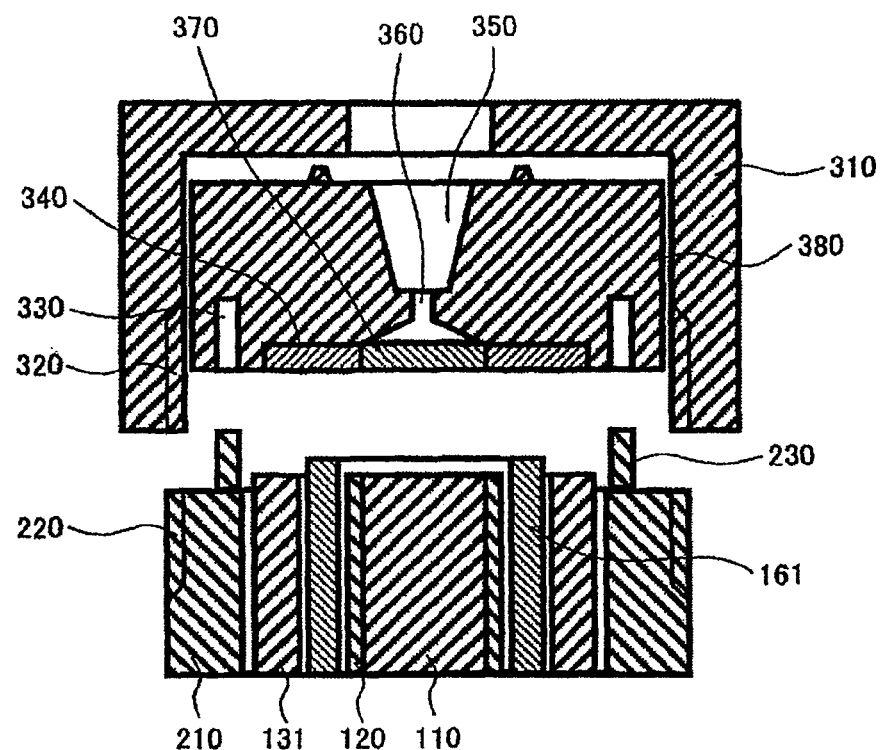
FIGS. 2A and 2B are sectional views on the sample inflow side of a separation column according to another embodiment.
Figure 2B:
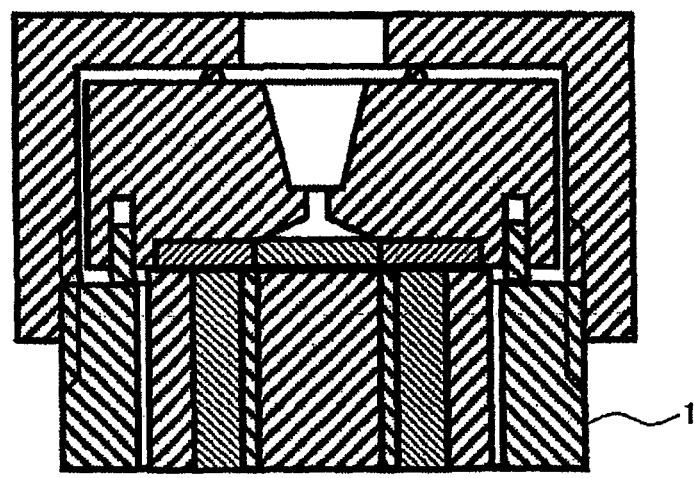

FIGS. 2A and 2B are sectional views of the sample inflow side of a separation column according to another embodiment.

The monolith rod 110 is coated with the coating material 120 and inserted into the support member 131. A solid filling material 161 for fixing the monolith rod is fitted into the gap between the coating material 120 and the support member 131.

The outer holder 210, the connecting member 380, the fixing member 310, etc. are the same as those of FIG. 1.

A solid member 161 is longer than the monolith rod 110 and the support member 131 by about 1 to 5 mm. When the threaded portions 220 and 320 of the outer holder 210 and the fixing member 310 are fastened, the packing 340 presses the end face of the solid member 161 to make sealing. As the solid member 161, it is preferable to use a molded product, TEFLON (registered trademark) or fluoride rubber processed after molding, or a highly chemical-resistant resin or rubber such as perfluoroelastomer.

Since the high-pressure liquid flowing into the monolith rod 110 is sealed by the packing 340 and the support member 131, the liquid does not leak outside the separation column 1.

As the solid member 161, a molded member or a member processed after molding is fitted into the gap between the monolith rod 110 coated with the coating material 120 and the support member 131. Therefore, before the separation column 1 is assembled, there are tight gaps between the coating material 120 and the solid member 161 and between the support member 131 and the solid member 161, as shown in FIG. 2A. When the separation column 1 is assembled, the solid member 161 vertically compressed by the packing 340 radially expands to fill the gaps, as shown in FIG. 2B. Thus, the solid member is firmly attached to the outer circumferential surface of the coating material 120 and the inner circumferential surface of the support member 131. When the solid member 161 radially expands, the coating material 120 is compressed toward the side of the monolith rod 110. Therefore, even if the high-pressure liquid flows in the monolith rod 110, the coating material 120 does not expand and the liquid does not leak into the gap between the monolith rod 110 and the coating material 120.

Therefore, in the manufacturing process of the separation column 1, it is possible to manufacture a separation column at such a low temperature that the octadecylsilyl group etc. does not drop off and use a highly chemical-resistant material as the solid member 161 fitted into the gap between the monolith rod 110 coated with the coating material 120 and the support member 130, resulting in no affections on separation. Further, even if the high-pressure liquid flows in the monolith rod 110, the liquid does not leak in the gap between the monolith rod 110 and the coating material 120.

Figure 3A:
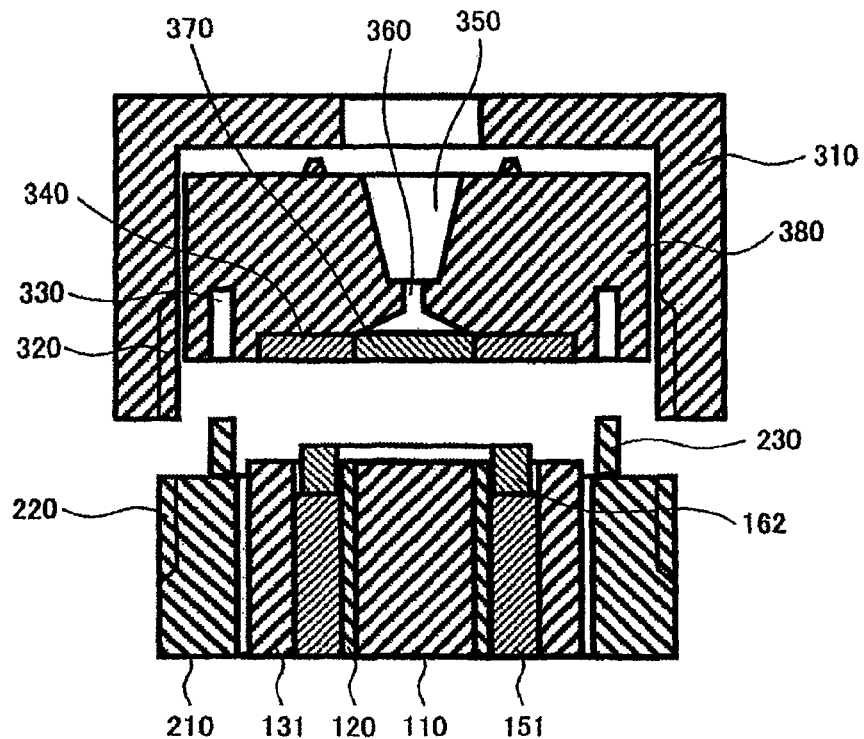
FIGS. 3A and 3B are sectional views on the sample inflow side of a separation column according to still another embodiment.
Figure 3B:
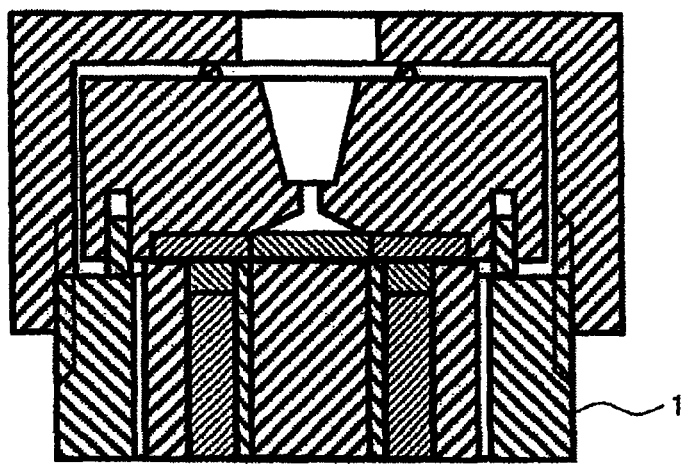

FIGS. 3A and 3B show separation column according to still another embodiment.

Referring to FIGS. 3A and 3B, the monolith rod 110 is coated with the coating material 120, and is inserted in the support member 131. The gap between the coating material 120 and the support member 131 is filled with the rod fixing material 151. A sealing member 162 is fitted to both ends (the inflow-side end in FIG. 3A) of the monolith rod 110 coated with the coating material 120.

The outer holder 210, the connecting member 380, the fixing member 310, etc. are the same as those of FIG. 1A.

As the rod fixing material 151, it is preferable to fill with fluid rubber, resin, glass, or metal; and then subject the material to dry hardening at such a low temperature that the octadecylsilyl group etc. are removed, for example, at about 200° C. Further, in order to cause the liquid to flow to the monolith rod 110 under high pressure, it is desirable to select a high-modulus material.

As the sealing member 162, it is preferable to use a molded product, TEFLON (registered trademark) or fluoride rubber processed after molding, or a highly chemical-resistant resin or rubber such as perfluoroelastomer.

As the sealing member 162, a molded member or a member processed after molding is fitted into the gap between the monolith rod 110 coated with the coating material 120 and the support member 131. Therefore, before the separation column 1 is assembled, there are tight gaps between the coating material 120 and the sealing member 162 and between the support member 131 and the sealing member 162, as shown in FIG. 3A. When the separation column 1 is assembled, the sealing member 162 vertically compressed by the packing 340 radially expands to fill the gaps, as shown in FIG. 3B. Thus, the sealing member is firmly attached to the outer circumferential surface of the coating material 120 and the inner circumferential surface of the support member 131.

Referring to FIGS. 2A and 2B, the longer the separation column is, the longer becomes the solid member 161. In this case, the radially expanding portion cannot be uniformed only by the compression force by the packing 340 at both ends, and therefore the solid member may not completely be attached to the outer circumferential surface of the coating material 120. In particular, therefore, when a long separation column is required, it is preferable to fill most of the gap between the coating material 120 and the support member 131 with a fluid rod fixing material 151, subject the material to dry hardening, and fit only to the end a molded sealing member 162 or the same processed after molding, as shown in FIG. 3A.

Since it is preferable to fit a short sealing member 162 only to the end, the gaps between the coating material 120 and the sealing member 162 and between the support member 131 and the sealing member 162 may be tight even in a condition before assembly shown in FIG. 3A. In particular, it is desirable that the outer circumferential surface of the coating material 120 and the inner circumferential surface of the sealing member 162 are slightly in contact with each other. When the gap is decreased in this manner, the sealing member 162 vertically compressed by the packing 340 radially expands to fill the gaps more securely after the separation column is assembled, as shown in FIG. 3B. This allows the sealing member to firmly be attached, in particular, to the outer circumferential surface of the coating material 120 and the inner circumferential surface of the support member 131.

The high-pressure liquid flowing inside the monolith rod 110 is sealed and does not leak outside the separation column 1 because of the adherence between the packing 340 and the support member 131. Further, the liquid does not come into contact with the rod fixing material 151 because of the adherence between the outer circumferential surface of the coating material 120 and the inner circumferential surface of the sealing member 162.

Figure 4:
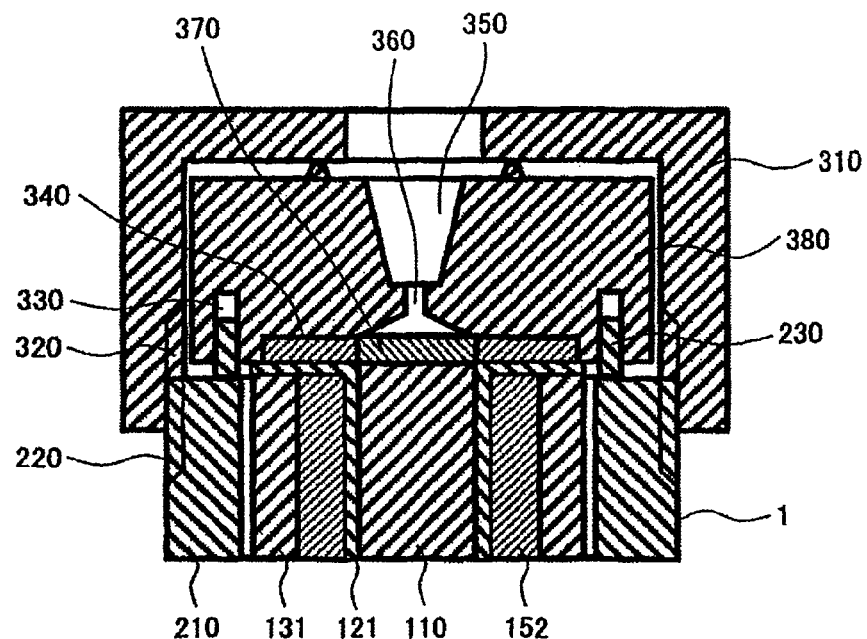
FIG. 4 is a sectional view on the sample inflow side of a separation column according to still another embodiment.

FIG. 4 shows a separation column according to still another embodiment.

The monolith rod 110 is coated with a coating material 121 and inserted into the support member 131. The gap between the coating material 121 and the support member 131 is filled with the rod fixing material 152.

The coating material 121 radially expands at both ends (the inflow-side end in FIG. 4) to coat the end of the rod fixing material 152 and the support member 131 when the separation column 1 is assembled.

The outer holder 210, the connecting member 380, the fixing member 310, etc. are the same as those of FIG. 1.

After the monolith rod 110 coated with the coating material 121 is inserted into the support member 131 and the gap filled with the rod fixing material 152, ends of the rod fixing material 152 and the support member 131 are coated. The coated end of the monolith rod 110 is polished. Alternatively, only the end of the monolith rod 110 is coated with a different material, the ends of the rod fixing material 152 and the support member 131 are coated with the coating material 121, and then the coat at the end of the monolith rod 110 is peeled off.

Figure 5:
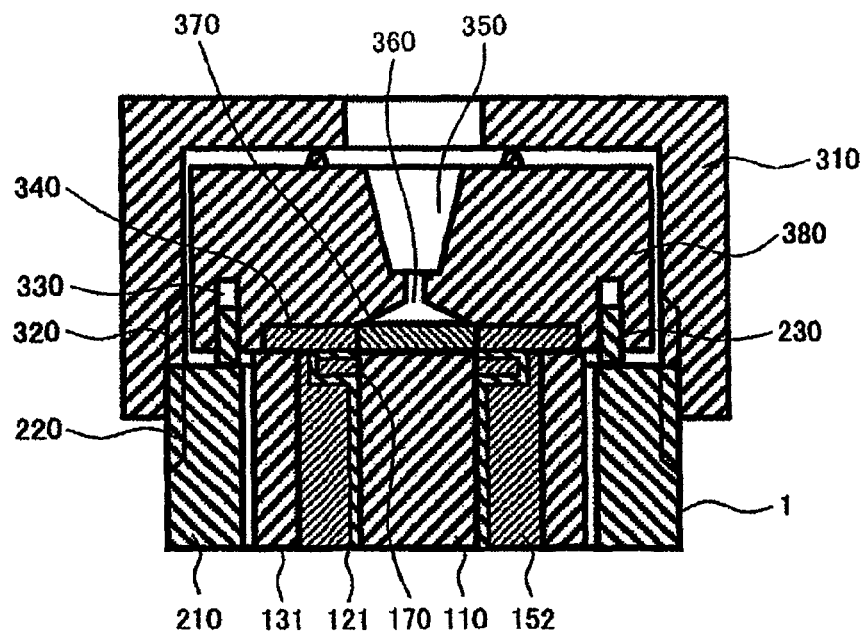
FIG. 5 is a sectional view on the sample inflow side of a separation column according to still another embodiment.

FIG. 5 shows a separation column according to still another embodiment.

A cylindrical member 170 is fitted to the end of the monolith rod 110 coated with the coating material 121 and is inserted into the support member 131. The gap between the coating material 121 and the support member 131 is filled with the rod fixing material 152.

The outer holder 210, the connecting member 380, the fixing member 310, etc. are the same as those of FIG. 1.

If the inner diameter of the cylindrical member 170 is almost the same as the outer diameter of the monolith rod 110 and therefore the cylindrical member is tightly fitted, the coating material 121 is not inserted into the inner circumference side of the cylindrical member 170. However, if the inner diameter of the cylindrical member 170 is larger than the outer diameter of the monolith rod 110, the coating material 121 is inserted into the gap between the cylindrical member 170 and a filling agent for separation 121, firmly fixing the cylindrical member 170 to the monolith rod 110.

After the monolith rod 110 and a seal ring 170 are coated with the coating material 121, the end of the filling agent for separation is polished.

Figure 6:
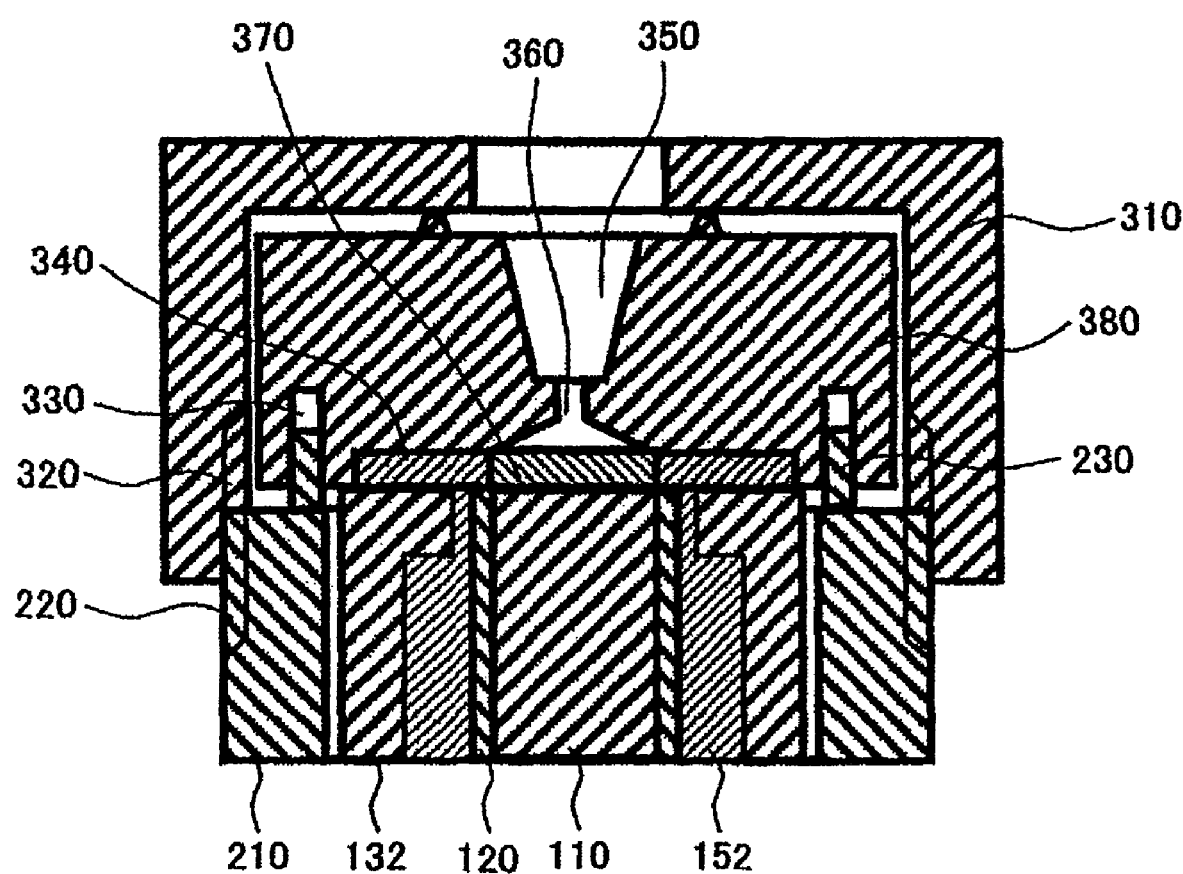
FIG. 6 is a sectional view on the sample inflow side of a separation column according to still another embodiment.

FIG. 6 shows a separation column according to still another embodiment.

The monolith rod 110 coated with the coating material 120 is inserted into the support member 132. The gap between the coating material 120 and the support member 132 is filled with the rod fixing material 152.

The outer holder 210, the connecting member 380, the fixing member 310, etc. are the same as those of FIG. 1.

The packing 340 is firmly attached to the end face of the rod fixing material 152 to make sealing. The degree of contact between the mobile phase flowing into the monolith rod 110 and the rod fixing material 152 can be reduced by reducing the inner diameter at the end of the support member 132 to reduce the end face area of the rod fixing material 152.

Since machining-level dimensional accuracy cannot be obtained with the surface of the monolith rod 110, the inner diameter of only the upper end of the support member 132 is reduced, i.e., made smaller than that of other portions, thus making it easier to insert the monolith rod 110 into the support member 132.

Even if the inner diameter of the end of the support member 132 is not reduced, the degree of contact between the mobile phase flowing into the monolith rod 110 and the rod fixing material 152 can be reduced by making the inner diameter of the packing 341 almost the same as the outer diameter of the monolith rod 110.

Further, like FIG. 4, it may be possible to radially expand the coating material 120 at both ends to coat end faces of the rod fixing material 152 and the support member 132 when the separation column 1 is assembled. This makes it possible to prevent the elution of chemical components from the rod fixing material 152 filled into the gap between the monolith rod 110 coated with the coating material 121 and the support member 132.

Figure 7A:
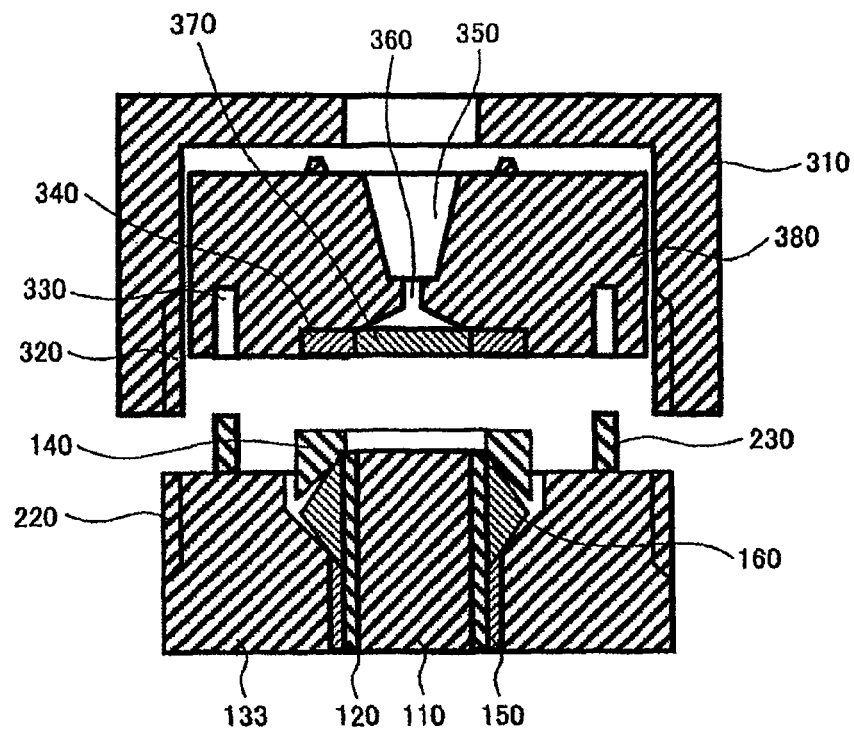
FIGS. 7A and 7B are sectional views on the sample inflow side of a separation column according to still another embodiment.
Figure 7B:
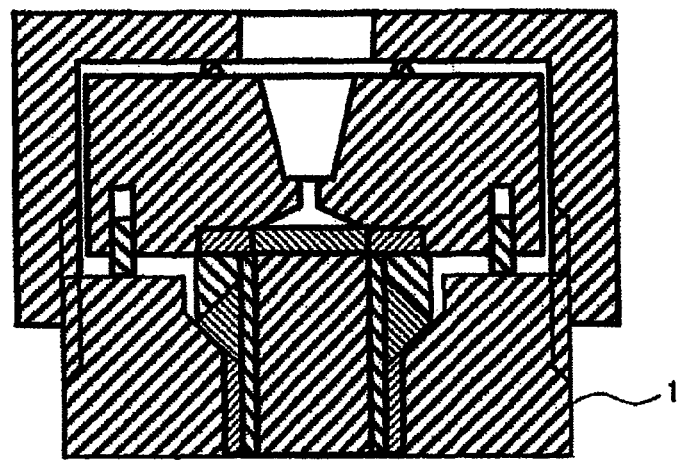

In the above explanations, the outer holder 210 having a threaded portion 220 and a projection 230 is provided on the outer circumference of the support members 130, 131, and 132. However, the number of parts can be reduced by integrating the support members with the outer holder. For example, FIGS. 7A and 7B show the separation column of FIG. 1A, wherein the support member 130 has been integrated with the outer holder 210 to form a support member 133. Therefore, in the manufacturing process of the separation column 1, it is possible to manufacture a separation column at such a low temperature that the octadecylsilyl group etc. are not removed and prevent to further extent the elution of chemical components from the rod fixing material 150 packed into the gap between the monolith rod 110 coated with the coating material 120 and the support member 133.

What is claimed is:

1. A monolith type separation column including a monolith rod which is cylindrically formed with a porous material and into which a sample and a mobile phase flow, the separation column comprising:

a coating material coated on the outer circumference of the monolith rod;

a support member into which the monolith rod coated with the coating material is inserted;

a rod fixing material filling a gap between the coating material and the support member;

a sealing member for preventing said sample from flowing into said rod fixing material, said sealing member having a tapered upper outer surface, a tapered lower outer surface, and an inner surface, and said sealing member contacting an outer peripheral surface of said coating material, an inflow-side end surface of said rod fixing material, an outflow-side end surface of said rod fixing material, and said support member to seal said inflow-side end surface and said outflow-side end surface of said rod fixing material; and a push-on member for pushing and pressing said sealing member toward said outer peripheral surface of said coating material, said inflow-side end surface of said rod fixing material, said outflow-side end surface of said rod fixing material, and said support member, said push-on member having a tapered inner surface that engages said tapered upper outer surface of said sealing member;

a diffusion member disposed on an upstream side of the monolith rod for introducing the sample to the monolith rod while allowing diffusion of the sample; and a packing member for pushing and pressing the push-on member toward said sealing member and having an inner circumference surrounding the diffusion member, wherein said rod fixing material is formed by inserting a fluid substance between said coating material and said support member and by hardening said fluid substance, and wherein said tapered inner surface of said push on member engages said tapered upper outer surface of said sealing member and presses said sealing member into contact with said outer peripheral surface of said coating material.

2. The separation column according to the claim 1, wherein:
the coating material is composed of a heat shrinkable tube or a fluid resin material, the rod fixing material is composed of silicon rubber or a thermoset resin, and the support member is composed of a stainless material.

3. The separation column according to the claim 1, wherein the outer diameter of the diffusion member is at least 0.8 times and at most 1.2 times the outer diameter of the monolith rod.

4. A liquid chromatograph that uses a monolith type separation column including a monolith rod into which a sample and a mobile phase flow,
wherein the separation column comprises:
a monolith rod cylindrically formed with a porous material;
a coating material coated on the outer circumference of the monolith rod;
a support member into which the monolith rod coated with the coating material is inserted;
a rod fixing filling a gap between the coating material and the support member;

a sealing member for preventing said sample from flowing into said rod fixing material, said sealing member having a tapered upper outer surface, a tapered lower outer surface, and an inner surface, and said sealing member contacting an outer peripheral surface of said coating material, an inflow-side end surface of said rod fixing material, an outflow-side end surface of said rod fixing material, and said support member to seal said inflow-side end surface and said outflow-side end surface of said rod fixing material; and a push-on member for pushing and pressing said sealing member toward said outer peripheral surface of said coating material, said inflow-side end surface of said rod fixing material, said outflow-side end surface of said rod fixing material, and said support member, said push-on member having a tapered inner surface that engages said tapered upper outer surface of said sealing member;

a diffusion member disposed on an upstream side of the monolith rod for introducing the sample to the monolith rod while allowing diffusion of the sample; and a packing member for pushing and pressing the push-on member toward said sealing member and having an inner circumference surrounding the diffusion member, wherein said rod fixing material is formed by inserting a fluid substance between said coating material and said support member and by hardening said fluid substance, and wherein said tapered inner surface of said push-on member engages said tapered upper outer surface of said sealing member and presses said sealing member into contact with said outer peripheral surface of said coating material.

5. A liquid according to claim 4, wherein the maximum pressure of the mobile phase flowing in the monolith rod is set to 5 to 30 Mpa.

6. A liquid chromatograph according to claim 4,
wherein the monolith rod has a diameter of 1.8 to 2.8 mm and a length of 30 mm to 200 mm; and
wherein the outer diameter of the diffusion member is at least 0.8 times and at most 1.2 times the outer diameter of the monolith rod.

7. A liquid chromatograph according to claim 4, wherein:
the coating material is composed of a heat shrinkable tube or a fluid resin material, the rod fixing material is composed of silicon rubber or a thermoset resin, and the support member is composed of a stainless material.

* * * * *